United States Patent [19]

Yang

[11] Patent Number: 4,540,828

[45] Date of Patent: Sep. 10, 1985

[54] CATALYSTS FOR ALKOXYLATION REACTIONS

[75] Inventor: Kang Yang, Ponca City, Okla.

[73] Assignee: Vista Chemical Company, Houston, Tex.

[21] Appl. No.: 469,550

[22] Filed: Feb. 25, 1983

Related U.S. Application Data

[62] Division of Ser. No. 383,387, Jun. 1, 1982, abandoned.

[51] Int. Cl.³ .............................................. C07C 41/03
[52] U.S. Cl. .................................. 568/616; 568/618; 568/619; 568/620; 568/675; 568/678; 568/680; 568/315; 568/386; 568/347; 568/433; 568/424; 568/485; 568/39; 564/123; 564/475; 560/263; 560/264; 560/112
[58] Field of Search .............. 568/616, 618, 619, 620, 568/622, 623, 675, 678, 680

[56] References Cited

U.S. PATENT DOCUMENTS

| | | | |
|---|---|---|---|
| 3,135,705 | 6/1964 | Vandenburg | 528/418 |
| 3,158,581 | 11/1964 | Vandenburg | 528/419 |
| 3,275,598 | 9/1966 | Garty et al. | 528/102 |
| 3,313,743 | 4/1967 | Filar et al. | 568/616 |
| 3,359,217 | 12/1967 | Brandner | 568/616 |
| 4,259,405 | 3/1981 | Newkirk et al. | 568/623 |

*Primary Examiner*—Howard T. Mars
*Attorney, Agent, or Firm*—Browning, Bushman, Zamecki & Anderson

[57] ABSTRACT

Catalysts and a method of using said catalysts for the alkoxylation of a variety of materials is disclosed. Catalysts so described produce alkoxylates having a very sharp alkoxylate distribution. The catalysts are supported and unsupported dialkoxy and dialkyl metal fluorides and halides and alkyl metal difluorides and dihalides.

2 Claims, 3 Drawing Figures

CATALYSTS FOR ALKOXYLATION REACTIONS

This is a division of application Ser. No. 383,387, filed June 1, 1982, now abandoned.

This invention relates to the production of alkoxylated organic compounds by reacting said compounds with an alkoxylating agent in the presence of dialkoxy and dialkyl metal fluorides, or chlorides or alkyl metal difluorides or dichlorides. More particularly, this invention relates to the production of alkoxylated organic compounds by reacting said compounds with the catalysts of the present invention in the presence of alkoxylating agents to yield a very sharply peaked alkoxylate distribution.

In general, the reaction of a variety of organic materials together with an adducting material such as ethylene oxide or propylene oxide to form alkoxylated materials is well known in the art. U.S. Pat. No. 2,683,087 discloses that water adsorption by paper articles is improved by the use of amine adducts of ethylene oxide. British Pat. No. 847,714 teaches the processing of prehydrolyzed sulfate wood pulp into viscose by incorporating a propylene oxide/ethylene oxide adduct of ethylene diamine. French Pat. No. 1,122,729 discloses the use of an acylarylpolyglycol adduct to the viscose pulp or slurry. Belgium Pat. No. 555,529 discloses an anti-static agent for synthetic fibers produced by esterifying one mole of lauric acid with one mole of an ethoxylated glycerol. British Pat. No. 763,215 suggests an ethoxylated organic sulfamide as an anti-static agent for textiles.

British Pat. No. 705,117 discloses an emulsifier combination for pesticides comprising a mixture including a tall oil or dodecyl mecaptan adduct. Polyhydric alcohol ethoxylates find uses in foods and feeds as shown by U.S. Pat. No. 2,674,534 which discloses the use of sorbitol laurate and sorbitol oleate adducts in the coating of ice cream bars. Alkylene oxide adducts are also used in the leather industry in formulations for tanning, dyeing, and lubricating leather. Adducts of organic materials also have a variety of uses and metal working industries where ester, ether and amine adducts are the products used most frequently. Ethylene oxide adducts such as sorbitan monostearate adducts have been found useful in pharmaceutical and cosmetic preparations and are used to provide activities such as drug carriers, emulsifiers and solubilizers. Ethylene oxide adducts of nonyl phenols have been used to produce detergents and cleaning agents, domestic and industrial laundry detergents, detergent builders, polishers, sanitizers, and dry cleaning materials. Alkyl phenol adducts are especially good soil suspending materials when used in detergent formulations since they possess excellent detergency, fat emulsifying power, concentration effect, chemical resistance, hard water stability and pH properties.

Much literature is available in the general area of alcohol alkoxylation. These references relate to the catalytic ability of various materials in the mechanism of kinetics of these reactions. For example, French Pat. No. 1,365,945 teaches the use of compounds containing an active hydrogen atom reacted with ethylene oxide in the presence of an alkali metal base.

Both basic and acidic catalysts in general are known to produce alkoxylation of organic materials. However, alkoxylation of these materials invariably produces a distribution of various adducts. For example, in surfactant applications, an adduct of too few ethylene oxide molecules is not effective because of poor solubility. In contrast, an adduct with too many ethylene oxide molecules is likewise undesirable because surface tension reduction per unit mass decreases drastically as the molecular weight increases. Thus it has long been essential to produce and use alkoxylates with as sharp a distribution in the desired mole adduct range for the particular use of the material as can possibly be realized.

Normally, acid catalyzed reactions produce such alkoxylates, but these catalysts produce harmful side products and must be separated and removed prior to use. Base catalysts normally do not produce by-products of acidic catalysts but provide a much broader distribution of alkoxylation adducts, thus making them economically unsuitable. Thus both methods have disadvantages.

Therefore, it would be desirable to provide a catalyst system for the alkoxylation of organic materials which provides low by-product levels, typical of base catalysts, yet provides a narrow distribution of the preferred mole adducts normally obtained from acid catalysts. Such a catalyst would promote the narrowing of product distribution curve and would contribute significantly to the intrinsic value of the alkoxylate produced.

Such a catalyst is described in U.S. Pat. Nos. 4,239,917 and 4,306,093. However, these catalysts, while effective in producing a very sharply peaked distribution product, do not produce as much peaking as the catalysts to be described herein.

The use of dialkyl aluminum fluoride or alkyl aluminum difluoride is known as a catalyst for the polymerization of epoxides to produce polyalkoxy alcohols as described in U.S. Pat. Nos. 3,029,216 and 3,313,743. However, these catalysts were not used in the alkoxylation of alcohols and require water, none of which is necessary in the present invention. In addition, dialkylaluminum halides or alkyl aluminum dihalides can be used to produce ethoxylated alcohols using different methods such as the polymerization of ethylene oxide as described in U.S. Pat. No. 3,321,533. However in this process the materials are not used as catalysts, but rather as reactants since sodium hydroxide acts as the ethoxylation catalyst.

U.S. Pat. No. 3,395,185 utilizes organoaluminum zinc compounds as catalysts in the preparation of low molecular weight polyoxymethylene glycols. Zinc, however, was not an effective catalyst in the present invention. U.S. Pat. No. 2,716,137 uses nitrogen containing catalysts. These materials are characterized by low reaction rates and objectionable odors. U.S. Pat. No. 4,282,387 uses catalysts such as calcium, strontium and barium acetates and naphthenates. These materials produce alkoxylate products more sharply peaked than commercially used basic catalysts such as sodium and potassium hydroxide, but do not provide the extremely high peaking of the present invention.

The ethoxylation of alcohols uing aluminum compounds such as aluminum trifluoride or trialkyl aluminum is described in U.S. Pat. Nos. 2,870,220; 3,350,462; 3,719,636 and 3,969,417.

It is therefore an object of the present invention to provide a catalyst system which will yield a narrow, alkylene oxide adduct distribution in the alkoxylation of organic materials, while providing low levels of undesirable by-products and non-desired alkoxylation adduct. Other objects will become apparent to those skilled in this art as the description proceeds.

It has now been discovered according to the instant invention that alkoxylation of organic material can be carried out in the presence of at least one catalyst having the general formula selected from the group consisting of

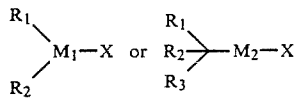

wherein X is a halogen selected from the group consisting of chlorine and fluorine, $R_1$, $R_2$ and $R_3$ are, independently, hydrogen, alkyl groups containing from 1 to 20 carbon atoms, alkoxide groups containing from 1 to 20 carbon atoms, and halogen, wherein at least one of $R_1$, $R_2$ or $R_3$ must be alkyl or alkoxide, and wherein $M_1$ is selected from the group consisting of aluminum, gallium, indium and thallium and $M_2$ is selected from the group consisting of titanium, zirconium and hafnium.

Representative but non-exhaustive examples of such catalysts are dialkylaluminum fluorides, alkylaluminum difluoride trialkyl zirconium fluorides, dialkyl zirconium difluoride, alkyl zirconium trifluorides, trialkyl titanium fluorides, dialkyl titanium fluorides, alkyl titanium difluorides, dialkoxy aluminum fluorides, alkoxy aluminum difluoride, trialkoxy zirconium fluorides, dialkoxy zirconium difluorides, alkoxy zirconium trifluorides, trialkoxy titanium fluorides, dialkoxy titanium difluorides, alkoxy titanium trifluorides, dialkoxy gallium fluorides, dialkoxy indium fluorides, dialkoxy thallium fluorides, and trialkoxy hafnium fluorides. These alkyl and alkoxy groups will normally contain from about 1 to about 20 carbon atoms, but the preferred catalysts are those containing from about 1 to about 14 carbon atoms.

DESCRIPTION OF THE PREFERRED EMBODIMENTS

Figure 1:
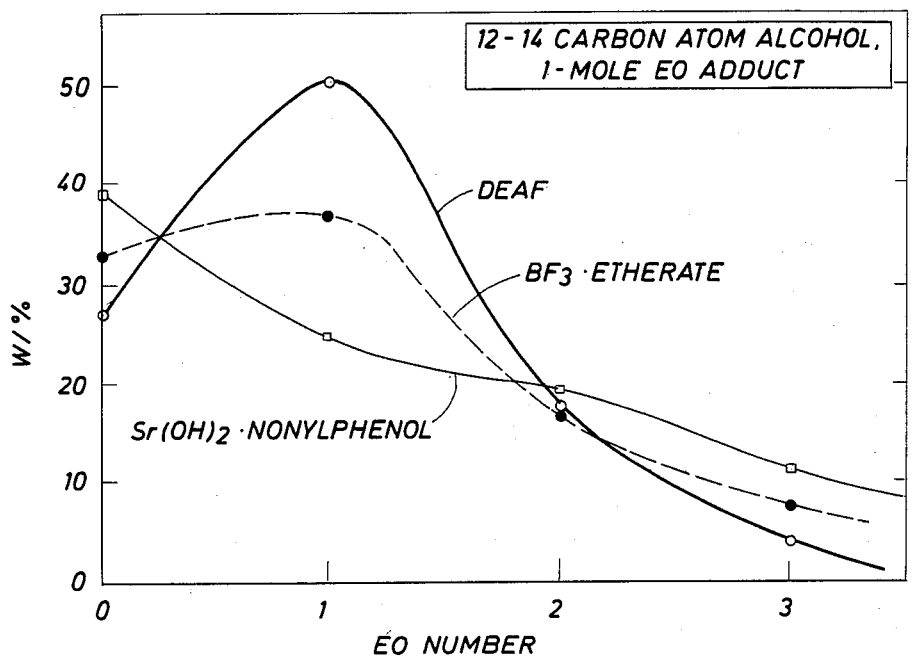
FIG. 1 is a graph showing ethoxylate distribution of alcohols ethoxylated using various catalysts.

The instant invention can be carried out at temperatures of from about 20° C. to about 260° C. However, more normal temperatures range from about 90° C. to about 200° C. For practical purposes, most commercial operations will be carried out in the temperature range of from about 100° C. to about 200° C.

The catalysts of the present invention can be used in processes carried out at ambient pressure. However, pressures above or below ambient can be carried out as desired. Pressure or lack of pressure is not a critical factor in the present invention and pressures may be used as convenient. Normally pressures of up to about 100 pounds per square inch (psig) can be used, but pressures below about 60 psig are preferred. It is simply more convenient to normally carry out the reactions in the pressure range of from about atmospheric to about 100 psig.

The alkoxylations of the present invention are normally carried out with materials or mixtures of materials comprising alpha and beta alkylene oxide. Of these materials, ethylene oxide, propylene oxide or mixtures of these are preferred. However, the process and catalysts of the present invention will be effective for any adducting material desired.

The reaction products can have any desired content of adducting material. For example, an alcohol alkoxylations ethylene oxide will normally comprise from about 30 to about 90% of product content based on weight. However, for most purposes the content of ethylene oxide will range from about 40% to about 70% by weight. The weight of adducting material present in the reaction is not critical other than the minimum amount necessary to provide sufficient units to reach the mole adduct level desired for the materials to be reacted.

For practical purposes, normally from about 0.05 to about 5.0 weight percent catalyst based upon the weight of the material to be reacted is present in the reaction. These catalysts are effective in the absence of promoters or cocatalysts, although promoters or cocatalysts can be used. Preferred levels of catalysts in the reaction mixture are from about 0.1 to about 1.0% by weight based on the total reaction mixture weight.

The catalysts of the present invention are normally added to the reaction mixture in a solution form. However, in order to render these catalysts less air sensitive and more stable, catalysts can optionally be supported on materials having active surface hydroxyl groups. Representative but non-exhaustive examples of such supports are alumina, diatomaceous earth, silica, bentonite glass, various clays and the like.

The catalysts of the present invention are useful for the alkoxylation of organic materials which can normally be alkoxylated. Among such materials are alcohols, whether polyhydric, unsaturated, linear or branched; saturated alcohols, alkyl phenols, polyols, aldehydes, ketones, amines, amides, organic acids and mercaptans.

These organic materials are normally selected from the group consisting of (a) polyols having a boiling point above 100° C. and containing a total of 2 to 30 carbon atoms; and having 2 or more hydroxyl containing compounds of the general formula

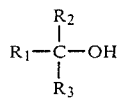

wherein $R_1$, $R_2$, and $R_3$ are, independently, linear or branched acyclic groups, alicyclic groups, aryl groups, cyclic groups, or hydrogen and wherein the R-designated groups can in addition contain one or more functional groups selected from the group consisting of amine, carboxyl, halogen, nitro, carbonyl, and amide;

(b) aldehydes and ketones having boiling points above 100° C. and containing a total of from 2 to 30 carbon atoms, and having one or more carbonyl containing compounds of the general formula

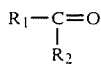

wherein R₁ and R₂ are, independently, hydrogen, linear or branched acyclic groups, alicyclic groups, cyclic groups, or aryl groups and wherein the R-designated groups can in addition contain one or more functionalities selected from the group consisting of carboxyl, hydroxyl, halogen, nitro, amine, or amide;

(c) primary, secondary or tertiary amides having a boiling point of above 100° C. and containing a total of from 1 to 30 carbon atoms and containing 1 or more amide containing compounds of the general formula

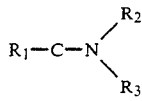

wherein R₁, R₂, and R₃ are, independently hydrogen, linear or branched acyclic groups, alicyclic groups, cyclic groups, or aryl groups and wherein the R-designated groups can in addition contain one or more other functionalities selected from the group consisting of hydroxyl, carboxyl, carbonyl, amine, nitro, or halogen;

(d) primary, secondary or tertiary amines having a boiling point above 100° C., containing from a total of 1 to 30 carbon atoms and containing 1 or more amine containing compounds of the general formula

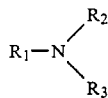

wherein R₁, R₂, and R₃ are, independently, hydrogen, liner or branched acyclic groups, alicyclic groups, cyclic groups, or aryl groups, and wherein the R-designated groups can in addition contain one or more functionalities selected from the group consisting of hydroxyl, carbonyl, halogen, carboxyl, nitro or amide;

(e) organic acids having a boiling point of above 100° C., containing from a total of 1 to 30 carbon atoms and having 1 or more carboxylic acid containing compounds of the general formula

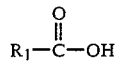

wherein R₁ is a hydrogen, a linear or branched acyclic group, alicyclic group, cyclic group, or aryl group and wherein the R group can in addition contain one or more functionalities selected from the group consisting of carbonyl, hydroxyl, halogen, nitro, amine, or amide;

(f) alkyl phenols hving a boiling point of above 100° C., containing a total of from 6 to 30 carbon atoms and having 1 or more compounds of the general formula

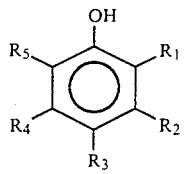

wherein R₁, R₂, R₃, R₄, and R₅ are, independently, hydrogen, halogen, hydroxyl, nitro, or carbonyl, linear or branched acyclic groups, alicyclic groups cyclic groups, aryl groups, or substituted aryl groups and wherein in addition the R-designated groups can contain one or more functionalities selected from the group consisting of halogen, ether, nitro, carboxyl, carbonyl, amine, amide, or hydroxyl;

(g) mercaptans of the general formula

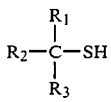

wherein R₁, R₂ and R₃ are, independently, hydrogen, linear or branched acyclic groups, alicyclic groups, cyclic groups or aryl groups containing from 1 to 30 carbon atoms and wherein the R₁, R₂ or R₃ designated groups can in addition contain one or more functionalities selected from the group consisting of carboxyl, hydroxyl, halogen, nitro amine, or amide, and (h) alcohols of the general formula

ROH where R is a linear or branched alkyl group containing from 1 to 30 carbon atoms, an aryl group or a cyclic group containing from 6 to 30 carbon atoms, or an olefinic or acetylenic group containing from 1 to 30 carbon atoms.

While the instant invention is effective with all classes of alcohols, both saturated and unsaturated, saturated alcohols are preferred. Of these, alkanols are most preferred. The alkanols primary, secondary linear and branched, linear and branched primary alkanols are the most commonly used and are the preferred materials for alkoxylation using the present invention.

Representative but non-exhaustive examples of alcohols which can be alkoxylated according to the present invention are 1-dodecanol; 1-tridecanol; 1-tetradecanol; 1-pentadecanol; 1-hexadecanol; 1-heptadecanol; 1-octadecanol; 1-nonadecanol; 1-eicosanol; 1-docosanol; 2-methyl-1-undecanol; 2-propyl-1-nonanol; 2-butyl-1-octanol; 2-methyl-1-tridecanol; 2-ethyl-1-dodecanol; 2-propyl-1-undecanol; 2-butyl-1-decanol; 2-pentyl-1-nonanol; 2-hexyl-1-octanol; 2-methyl-1-pentadecanol; 2-ethyl-1-tetradecanol; 2-propyl-1-tridecanol; 2-butyl-1-dodecanol; 2-pentyl-1-undecanol; 2-hexyl-1-decanol; 2-heptyl-1-decanol; 2-hexyl-1-nonanol; 2-octyl-1-octanol; 2-methyl-1-heptadecanol; 2-ethyl-1-hexadecanol; 2-propyl-1-pentadecanol; 2-butyl-1-tetradecanol; 1-pentyl-1-tridecanol; 2-hexyl-1-dodecanol; 2-octyl-1-decanol; 2-nonyl-1-nonanol; 2-dodecanol; 3-dodecanol; 4-dodecanol; 5-dodecanol; 6-dodecanol; 2-tetradecanol; 3-tetradecanol; 4-tetradecanol; 5-tetradecanol; 6-tetradecanol; 7-tetradecanol; 2-hexadecanol; 3-hexadecanol; 4-hexadecanol; 5-hexadecanol; 6-hexadecanol; 7-hexadecanol; 8-hexadecanol; 2-octadecanol; 3-octadecanol; 4-octadecanol; 5-octadecanol; 6-octadecanol; 7-octadecanol; 8-octadecanol; 9-octadecanol; 9-octadecenol-1; 2,4,6-trimethyl-1-heptanol; 2,4,6,8-tetramethyl-1-nonanol; 3,5,5-trimethyl-1-hexanol; 3,5,5,7,7-pentamethyl-1-octanol; 3-butyl-1-nonanol; 3-butyl-1-undecanol; 3-hexyl-1-undecanol; 3-hexyl-1-tridecanol; 3-octyl-1-tridecanol; 2-methyl-2-undecanol; 3-methyl-3-undecanol; 4-methyl-4-undecanol; 2-methyl-2-tridecanol; 3-methyl-3-tridecanol; 4-methyl-3-tridecanol; 4-methyl-4-tridecanol; 3-ethyl-3-decanol; 3-ethyl-3-dodecanol; 2,4,6,8-tetramethyl-2-nonanol; 2-methyl-3-undecanol; 2-methyl-4-undecanol; 4-methyl-2-undecanol; 5-methyl-2-undecanol; 4-ethyl-2-decanol; 4-ethyl-3-decanol; tetracosanol; hexacosanol; octacosanol; triacontanol; dotriacontanol; hexatriacontanol; 2-decyltetradecanol; 2-dodecylhexadecanol; 2-tetradecyloctadecanol; 2-hexadecyleicosanol, and unsaturated alcohols such as 1-hexyn-3-ol; 4-ethyl-1-octyn-3-ol; 2-methyl-3-butyn-2-ol; 3-methyl-1-pentyn-3-ol; oleyl alcohol (technically named cis-9-octadecene 1-ol); 2,5-dimethyl-4-octyne-3,6-diol; 2,4,7,9-tetramethyl-n-decyne-4,7-diol; 3-dodecene-1-ol; and 3,6-dimethyl-8-dodecene-1-ol.

Representative but non-exhaustive examples of various polyols which can be alkoxylated according to the present invention are:
ethylene glycol
1,2-propylene glycol
1,4-butanediol
1,6-hexanediol
1,10-decanediol
1,3-butylene glycol
diethylene glycol
diethylene glycol monobutyl ether
diethylene glycol monomethyl ether
diethyl glycol monoethyl ether
dipropylene glycol
dipropylene glycol monomethyl ether
ethylene glycol monomethyl ether
ethylene glycol monoethyl ether
ethylene glycol monobutyl ether
hexylene glycol
mannitol
sorbitol
pentaerythritol
dipentaerythritol
tripentaerythritol
trimethylolpropane
trimethylolethane
neopentyl glycol
diethaholamine
triethanolamine
diisopropanolamine
triisopropanolamine
1,4-dimethylolcyclohexane
2,2-bis(hydroxymethyl)propionic acid
1,2-bis(hydroxymethyl)benzene
4,5-bis(hydroxymethyl)furfural
4,8-bis(hydroxymethyl)tricyclo[5,2,1,0]decane
tartaric acid
2-ethyl-1,3-hexanediol
2-amino-2-ethyl-1,3-propanediol
triethylene glycol
tetraethylene glycol
glycerol
ascorbic acid Representative but non-exhaustive examples of various aldehydes and ketones which can be alkoxylated according to the present invention are
lauryl aldehyde
benzaldehyde
2-undecanone
acetophenone
2,4-pentandione
acetylsalicyclic acid
ortho-chlorobenzaldehyde
para-chlorobenzaldehyde
cinnamic aldehyde
diisobutyl ketone
ethylacetoacetate
ethyl amyl ketone
camphor
para-hydroxybenzaldehyde
2-carboxybenzaldehyde
4-carboxybenzaldehyde
salicylaldehyde
octyl aldehyde
decyl aldehyde
p-methoxybenzladehyde
p-aminobenzaldehyde
phenylacetaldehyde
acetoacetic acid
2,5-dimethoxybenzaldehyde
1-naphthyl aldehyde
terephthaldehyde Representative but non-exhaustive examples of amides which can be alkoxylated according to the instant invention are:
formamide
benzamide
acetanilide
salicylamide
acetoacetanilide
ortho-acetoacetotoluidide
acrylamide
N,N-diethyltoluamide
N,N-dimethylacetamide
N,N-dimethylformamide
phthalimide
octylamine
decylamine
laurylamide
stearylamide
N,N-dimethylollaurylamide
N,N-dimethylacrylamide
para-chlorobenzamide
para-methoxybenzamide
para-aminobenzamide
para-hydroxybenzamide
ortho-nitrobenzamide
N-acetyl-para-aminophenol
2-chloroacetamide
oxamide
N,N-methylene-bis-acrylamide Representative but non-exhaustive examples of amines which can be alkoxylated according to the present invention are:
aniline
benzylamine
hexadecylamine
triphenylamine
aminoacetic acid
anthranilic acid cyclohexylamine
tert-octylamine
ortho-phenylenediamine
meta-phenylenediamine
para-phenylenediamine
N-acetyl-para-aminophenol
2-amino-4-chlorophenol
2-amino-2-ethyl-1,3-propanediol
ortho-aminophenol
para-aminophenol
para-aminosalicylic acid
benzyl-N,N-dimethylamine
tert-butylamine
2-chloro-4-aminotoluene
6-chloro-2-aminotoluene
meta-chloroaniline
ortho-chloroaniline
para-chloroaniline
4-chloro-2-nitroaniline
cyclohexylamine
dibutylamine
2,5-dichloroaniline
3,4-dichloroaniline
dicyclohexylamine
diethanolamine
N,N-diethylethanolamine
N,N-diethyl-meta-toluidine
N,N-diethylaniline
diethylenetriamine
diisopropanolamine
N,N-dimethylethanolamine
N,N-dimethylaniline
2,4-dinitroaniline
diphenylamine
ethyl-para-aminobenzoate
N-ethylethanolamine
N-ethyl-1-naphthylamine
N-ethyl-ortho-toluidine
N-ethylaniline
ethylenediamine
hexamethylenetetraamine 2,4-lutidine
N-methylaniline
methyl anthranilate
p,p'-diaminodiphenyl methane
ortho-nitroaniline
para-nitroaniline
tert-octylamine
piperazine
ethanolamine
isopropanolamine
ortho-toluidine
para-toluidine
2,4-tolyenediamine
triethanolamine
tributylamine
triisopropanolamine
2,4-dimethylxylidine
para-methoxyaniline
nitrilotriacetic acid
N-phenyl-1-naphthylamine Representative but non-exhaustive examples of organic acids which can be alkoxylated according to the present invention are:
formic acid
acetic acid
valeric acid
heptanoic acid
2-ethylhexanoic acid
lauric acid
stearic acid
oleic acid
tall oil acids
hydrogenated tall oil acids
benzoic acid
salicyclic acid
adipic acid
azelaic acid
fumaric acid
citric acid
acrylic acid
aminoacetic acid
para-aminosalicylic acid
anthranilic acid
butyric acid
propionic acid
ricinoleic acid
chloroacetic acid
ortho-chlorobenzoic acid
2,4-dichlorophenoxyacetic acid
tert-decanoic acid
para-aminobenzoic acid
abietic acid
itaconic acid
lactic acid
glycolic acid
malic acid
maleic acid
cinnamic acid
para-hydroxybenzoic acid
methacrylic acid
oxalic acid
myristic acid
palmitic acid
tert-pentanoic acid
phenylacetic acid
mandelic acid
sebacic acid
tallow fatty acids
hydrogenated tallow fatty acids
tartaric acid
trichloroacetic acid
2,4,5-trichlorophenoxyacetic acid
undecylenic acid
crotonic acid
pelargonic acid
acetoacetic acid
para-nitrobenzoic acid
ascorbic acid
nitrilotriacetic acid
naphthenic acids
1-naphthoic acid
trimellitic acid Representative but non-exhaustive examples of various phenols which can be alkoxylated according to the present invention are
phenol
ortho-cresol
meta-cresol
para-cresol
2,4-dimethylphenol
2,5-dimethylphenol
2,6-dimethylphenol
ortho-chlorophenol
meta-chlorophenol
para-chlorophenol
para-nitrophenol para-methoxyphenol
salicylic acid
meta-hydroxyacetophenone
para-aminophenol
ortho-phenylphenol
nonylphenol
octylphenol
t-butyl-para-cresol
hydroquinone
catechol
resorcinol
pyrogallol
1-naphthol
2-naphthol
4,4'-isopropylidenediphenol (bisphenol A)
methyl salicylate
benzyl salicylate
4-chloro-2-nitrophenol
para-t-butylphenol
2,4-di-t-amylphenol
2,4-dinitrophenol
para-hydroxybenzoic acid
8-hydroxyquinoline
methyl para-hydroxybenzoate
2-nitro-para-cresol
ortho-nitrophenol
para-phenylphenol
phenyl salicylate
salicylaldehyde
p-hydroxy benzaldehyde
2-amino-4-chlorophenol
ortho-aminophenol
salicylamide The invention is more concretely described with reference to the examples below wherein all parts and percentage are by weight unless otherwise specified. The examples are provided to illustrate the present invention and not to limit it.

EXAMPLE 1

Diethylaluminum fluoride (DEAF) was used as an ethoxylation catalyst. ALFOL 1214 alcohol (a 12-14 carbon atom alcohol, trademark of and sold by CONOCO Inc.) in the amount of 300 grams was mixed with 10 cubic centimeters at 25% diethylaluminum fluoride in heptane. The mixture was degassed for 30 minutes at 150° C. with nitrogen purging at a rate of 500 cubic centimeters per minute. After evacuation, 64 grams of ethylene oxide was introduced at about 40 pounds per square inch gauge (psig) pressure at 150° C. The reaction mixture was cooled to 100° C. whereafter 5 grams of calcium hydroxide was added. Fifteen minutes agitation followed at which time the reaction mixture was filtered. Distribution of the product alkoxylated alcohol was determined by using high pressure liquid partition liquid chromatography. The distribution in shown in FIG. 1.

EXAMPLE 2

As a comparative example a known BF$_3$/etherate catalyst was tested. 300 grams of an ALFOL 1214 alcohol was mixed with 2 cubic centimeters BF$_3$ etherate. The mixture was heated to 50° C. and was evacuated briefly at this temperature. As an ethoxylating agent 64 grams of ethylene oxide was introduced at about 3 pounds per square inch gauge at 50°-60° C. The distribution was again determined using high pressure liquid partition chromatography and the results are set forth in FIG. 1.

EXAMPLE 3

A strontium hydroxide nonyl phenol promoted catalyst as described in U.S. Pat. No. 4,223,164 was prepared by mixing 67,857 grams of ALFOL 1214 alcohol, 55,071 grams of nonylphenol and 15,003 grams of strontium hydroxide. 5 grams of resulting catalyst was mixed with 300 grams of ALFOL 1214 alcohol and a reaction was carried out at 170° C. in 40 psig. After introducing 64 grams of ethylene oxide the product was cooled to 100° C. and neutralized with carbon dioxide. The distribution was determined using high pressure liquid partition chromatography. The results are set forth in FIG. 1.

EXAMPLE 4

Figure 2:
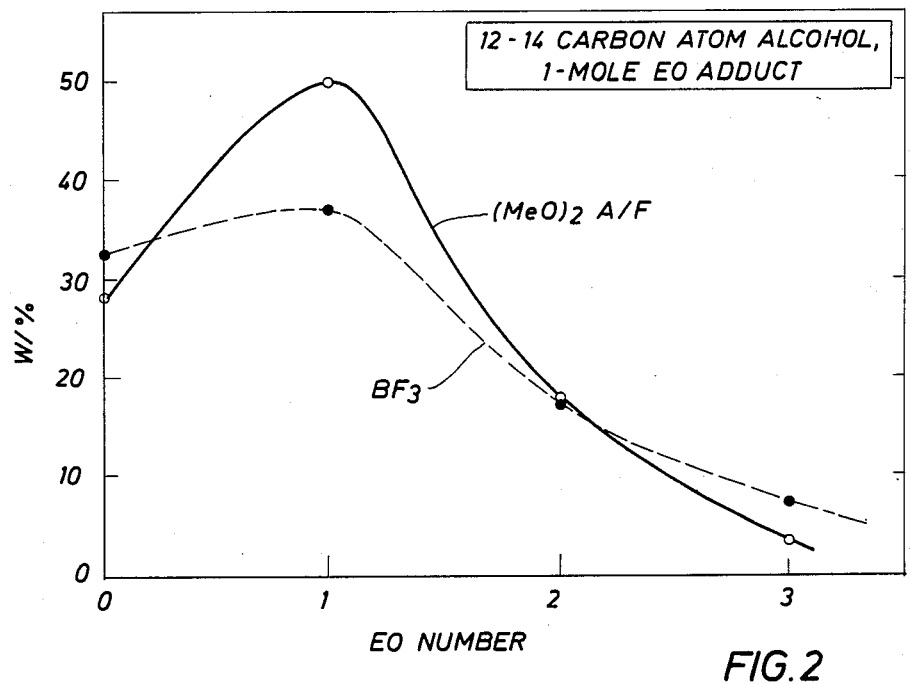
FIG. 2 is a graph similar to FIG. 1 showing ethoxylate distribution of alcohols using still other catalysts.

A mixture of 50 cubic centimeters of methanol and 10 cubic centimeters of 25% diethylaluminum fluoride in hexane was refluxed 30 minutes, then rotary dried to remove excess methanol. The catalyst together with 300 grams of ALFOL 1214 alcohol was purged with nitrogen at 500 cubic centimeters per minute for 30 minutes at a temperature of 150° C. After a brief evacuation 64 grams of ethylene oxide was introduced at 40 psig and 150° C. and allowed to react for 135 minutes. The distribution was obtained using high pressure liquid partition chromatography. Distribution is set forth in FIG. 2.

EXAMPLE 5

The effectiveness of support on the catalyst was determined, by mixing 5 grams of silica gel with 10 cubic centimeters of 25% diethylaluminum fluoride in hexane. The mixture was rotary dried to remove hexane. The resulting catalyst was used with 300 grams of ALFOL 1214 alcohol and the ethoxylation carried out as described in Example 4. As an alkylating agent 118 grams of ethylene oxide was introduced over 280 minutes. The product contained 5.2% unreacted alcohol.

Figure 3:
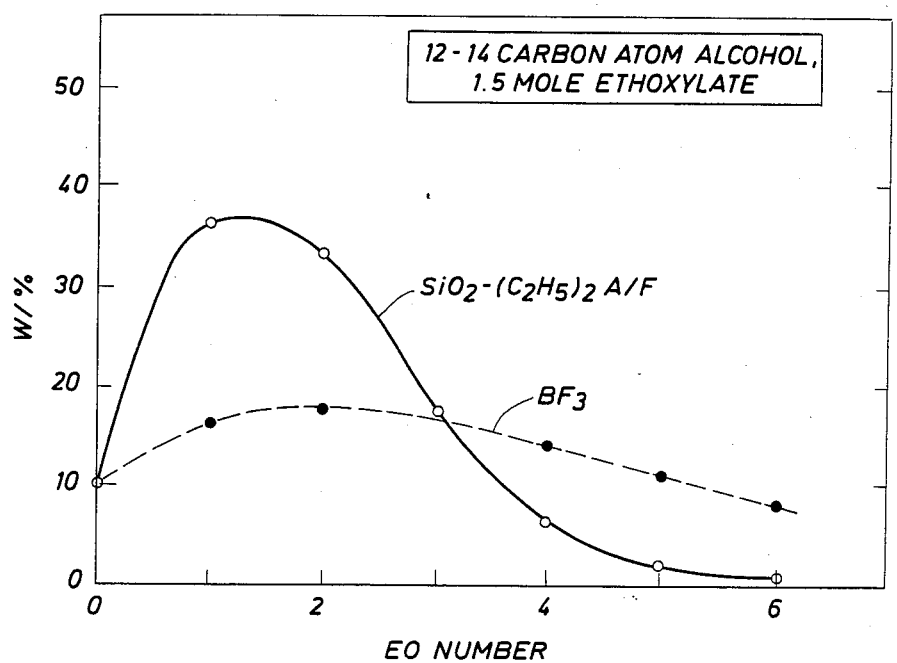
FIG. 3 is a graph similar to FIGS. 1 and 2 showing the use of still other catalysts and different mole ratios of alcohol to ethoxylate adduct.

A comparative experiment was carried out using BF$_3$ to produce the product with the same free alcohol level. The results are summarized in FIG. 3, clearly showing the higher peaking obtained using the silica supported diethyl aluminum fluoride catalyst.

COMPARATIVE EXAMPLE 6

An experiment as in Example 1 is performed with 2 grams of dibutyl zinc. No measurable ethoxylation occurred.

While certain embodiments and details have been shown for the purpose of illustrating this invention, it will be apparent to those skilled in this art that various changes and modifications may be made herein without departing from the spirit or scope of the invention.

I claim:

1. A method for the alkoxylation of an alcohol to yield a sharply peaked alkoxylate distribution comprising contacting, in the absence of water said alcohol with an alkoxylating agent in the presence of a catalyst comprising at least one material of the general formula

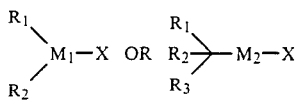

at a temperature of about 25° C. to about 200° C. for a time sufficient to alkoxylate to the extent desired, wherein x is a halogen selected from the group consisting of chlorine and fluorine, $R_1$, $R_2$ and $R_3$ are, independently, hydrogen, alkyl groups containing from 1 to 20 carbon atoms, alkoxide groups containing from 1 to 20 carbon atoms, and halogen, wherein at least one of $R_1$, $R_2$ or $R_3$ must be alkyl or alkoxide, wherein $M_1$ is selected from the group consisting of aluminum, gallium, indium and thallium and $M_2$ is selected from the group consisting of titanium, zirconium and hafnium.

2. A method for the ethoxylation of alcohols to yield a sharply peaked alkoxylate distribution comprising contacting in the absence of water said alcohols with ethylene oxide in the presence of a catalyst containing at least one material of the general formula

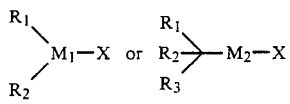

at a temperature of about 25° C. to about 200° C. for a time sufficient to alkoxylate to the extent desired, wherein at least one of $R_1$, $R_2$ or $R_3$ must be alkyl or alkoxide, wherein $M_1$ is selected from the group consisting of aluminum gallium, indium and thallium and $M_2$ is selected from the group consisting of titanium, zirconium and hafnium, and wherein the alcohol ethoxylate is at least one alcohol selected from the group consisting of 1-dodecanol; 1-tridecanol; 1-tetradecanol; 1-pentadecanol; 1-hexadecanol; 1-heptadecanol; 1-octadecanol; 1-nonadecanol; 1-eicosanol; 1-docosanol; 2-methyl-1-undecanol; 2-propyl-1-nonanol; 2-butyl-1-octanol; 2-methyl-1-tridecanol; 2-ethyl-1-dodecanol; 2-propyl-1-undecanol; 2-butyl-1-decanol; 2-pentyl-1-nonanol; 2-hexyl-1-octanol; 2-methyl-1-pentadecanol; 2-ethyl-1-tetradecanol; 2-propyl-1-tridecanol; 2-butyl-1-dodecanol; 2-pentyl-1-undecanol; 2-hexyl-1-decanol; 2-heptyl-1-decanol; 2-hexyl-1-nonanol; 2-octyl-1-octanol; 2-methyl-1-heptadecanol; 2-ethyl-1-hexadecanol; 2-propyl-1-pentadecanol; 2-butyl-1-tetradecanol; 1-pentyl-1-tridecanol; 2-hexyl-1-dodecanol; 2-octyl-1-decanol; 2-nonyl-1-nonanol; 2-dodecanol; 3-dodecanol; 4-dodecanol; 5-dodecanol; 6-dodecanol; 2-tetradecanol; 3-tetradecanol; 4-tetradecanol; 5-tetradecanol; 6-tetradecanol; 7-tetradecanol; 2-hexadecanol; 3-hexadecanol; 4-hexadecanol; 5-hexadecanol; 6-hexadecanol; 7-hexadecanol; 8-hexadecanol; 2-octadecanol; 3-octadecanol; 4-octadecanol; 5-octadecanol; 6-octadecanol; 7-octadecanol; 8-octadecanol; 9-octadecanol; 9-octadecenol-1; 2,4,6-trimethyl-1-heptanol; 2,4,6,8-tetramethyl-1-nonanol; 3,5,5-trimethyl-1-hexanol; 3,5,5,7,7-pentamethyl-1-octanol; 3-butyl-1-nonanol; 3-butyl-1-undecanol; 3-hexyl-1-undecanol; 3-hexyl-1-tridecanol; 3-octyl-1-tridecanol; 2-methyl-2-indecanol; 3-methyl-3-undecanol; 4-methyl-4-undecanol; 2-methyl-2-tridecanol; 3-methyl-3-tridecanol; 4-methyl-3-tridecanol; 4-methyl-4-tridecanol; 3-ethyl-3-decanol; 3-ethyl-3-dodecanol; 2,4,6,8-tetramethyl-2-nonanol; 2-methyl-3-undecanol; 2-methyl-4-undecanol; 4-methyl-2-undecanol; 5-methyl-2-undecanol; 4-ethyl-2-decanol; 4-ethyl-3-decanol; tetracosanol; hexacosanol; octacosanol; triacontanol; dotriacontanol; hexatriacontanol; 2-decyltriacontanol; dotriacontanol; hexatriacontanol; 2-decyltetradecanol; 2-dodecylhexadecanol; 2-tetradecyloctadecanol; 2-hexadecyleicosanol; and unsaturated alcohols such as 1-hexyn-3-ol; 4-ethyl-1-octyl-3-ol; 2-methyl-3-butyn2-ol; 3-methyl1-pentyn-3-ol; oleyl alcohols (technically named cis-9-octadecene-1-ol); 2,5-dimethyl-4-octyne-3,6-diol; 2,4,7,9-tetramethyl-4-decyne-4,7-diol; 3-dodecene-1-ol; and 3,6-dimethyl-8-dodecene-1-ol.

* * * * *